US009997259B1

(12) United States Patent
Spaulding

(10) Patent No.: US 9,997,259 B1
(45) Date of Patent: Jun. 12, 2018

(54) IN STORE MEDICAL DIAGNOSTICS

(71) Applicant: Glenn Spaulding, Houston, TX (US)

(72) Inventor: Glenn Spaulding, Houston, TX (US)

(*) Notice: Subject to any disclaimer, the term of this patent is extended or adjusted under 35 U.S.C. 154(b) by 861 days.

(21) Appl. No.: 14/305,142

(22) Filed: Jun. 16, 2014

Related U.S. Application Data

(60) Provisional application No. 61/837,714, filed on Jun. 21, 2013.

(51) Int. Cl.
*G16H 10/40* (2018.01)
*G06F 19/00* (2018.01)
*G06Q 30/04* (2012.01)
*A61B 5/15* (2006.01)

(52) U.S. Cl.
CPC .............. *G16H 10/40* (2018.01); *A61B 5/15* (2013.01); *G06F 19/366* (2013.01); *G06Q 30/04* (2013.01)

(58) Field of Classification Search
CPC .......... G06Q 50/22; G06Q 50/24; G16H 10/40
See application file for complete search history.

(56) References Cited

U.S. PATENT DOCUMENTS

| 2008/0228107 | A1* | 9/2008 | Reddy | ............... | G06Q 50/22 |
| | | | | | 600/584 |
| 2009/0061450 | A1* | 3/2009 | Hunter | ............ | B01L 3/502715 |
| | | | | | 435/6.11 |

FOREIGN PATENT DOCUMENTS

WO    WO-2014190052 A2 *  11/2014  ............. G06Q 50/22

* cited by examiner

*Primary Examiner* — Robert A Sorey
*Assistant Examiner* — Kristine K Rapillo

(57) ABSTRACT

Health care costs must be extremely lowered, and the business manner by which it is distributed simplified for the average person. A business method is described that allows the average person to obtain their own blood tests while shopping at a local store. Diagnostics for cancer, heart disease, infection, liver disease, kidney disease, hormonal imbalance, and many other maladies can be ascertained.

6 Claims, 2 Drawing Sheets

IN STORE MEDICAL DIAGNOSTICS

CROSS-REFERENCE TO RELATED APPLICATIONS

This application fully incorporates Application No. U.S. 61/837,714 and claims all current and prior rights.

STATEMENT REGARDING FEDERALLY SPONSORED RESEARCH OR DEVELOPMENT

Not Applicable.

REFERENCE TO A "MICROFICHE APPENDIX"

Not Applicable.

NOTICE OF MATERIAL SUBJECT TO COPYRIGHT PROTECTION

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

BACKGROUND OF THE INVENTION

1. Field of the Invention

Health care is very expensive and is consuming increasing portions of the average person's monthly income. Yet, individual care and attention to the individual's needs, house calls, family visits, privacy, personal relationships, and immediate access to your physician have been severely reduced or eliminated. The business interface that distributes medicine to the average person is overwhelmed with regulatory requirements and business structure practices. Regulatory requirements and business structure practices impose substantial cost burdens on the business interface that distributes medicine. Just a few of those burdens include: medical taxes, medical device taxes, licensed personnel, licensed personnel to support licensed personnel, yearly certifications, yearly state dues, training certifications, facilities certifications, special facilities insurance, malpractice insurance for all the individuals involved, litigation insurance for all the institutes involved, and may more financial burdens. Less than one hundred years ago the average person's health care cost was insignificant. They were responsible for themselves. They went to the doctor. They went for tests. They obtained their own medicine (there was no such thing as a required drug prescription to purchase medicine). The herein disclosed business method embodies instrumentation towards an information transformation that enables the average individual to again manage their own health care, and eliminates the financial burdens imposed by the middlemen.

2. Description of the Related Art

Definitions

Stain—refers to a chemical used to highlight cell, cellular constituents, and extracellular structures specifically for imaging. Indicator or Reagent—refers to a chemical reactant targeted to a specific substrate analysis, and applicable to non-imaging analytics. Indicators can include but are not limited to enzymes, antibodies, aptamers, RNA, DNA, PCR, gold beads, nano-indicators, and others that have sensitivities to whole blood constituents that are known in the art.

Diagnostic indicators in hospitals require a large test tube blood collections. Those indicators are often referred to a blood panel. Due to the extensive complexities, equipment and skilled personnel requirements, they are not FDA CLIA waiverable. Panels refer to two or more tests for specific whole blood constituents.

SUMMARY OF THE INVENTION

A simple finger stick by methods known in the art is all it takes to collect a whole blood sample. Average adults and children are capable of collecting a drop of whole blood. Dispensing the drop of blood to a surface with a sensor behind that surface eliminates many of the professional costs such as phlebotomists. Deposed to the surface where the whole blood resides are reactants. The reactants are known in the art and respond to serum constituents in a predictable manner. In one embodiment, the response is a colorimetric change. One or more photonic sensors distinguish the response and software transforms that information into a contextual construct that is understandable to the average person. That contextual construct can range from, but is not limited to, 'you are healthy' to 'your xxx is abnormal see a physician'. The sample collection, processing, billing, and information display are disclosed as a low cost solution for improved healthcare.

In one embodiment of the invention, a store kiosk provides access to healthcare diagnostics of whole blood constituents, including methods for collection and billing.

In one embodiment of the invention, a cell phone is linked to a disposable or low cost diagnostic means therein providing access to healthcare diagnostics of whole blood constituents, including methods for collection and billing.

In one embodiment of the invention, a transparent diagnostic means in conjunction with photonic sensing means provides access to healthcare diagnostics for whole blood parasites, including methods for collection and billing.

DETAILED DESCRIPTION OF THE INVENTION

It is known in the art that whole blood can be collected from any vascular bed in the body. Finger stick sampling evolved due to ease, accessibility and cultural influences. Pens with sharp spring loaded pins and laser ablation are the most common methods. Laser ablation and sampling has the lowest incidence of pain but at the highest cost. The current invention uses either systems of collection.

Whole blood from the collection is deposed to a surface. In the finger stick embodiment, whole is collected by depressing the blood droplet against a designated area indicated by the kiosk or the area graphically indicated on the cell phone accessory. Blood adherent to the surface is then used for further serum constituent analysis.

An outer wall is then juxtapositioned over the blood adherent surface to block incoming stray light that may interfere with sensor readings. Said sensor being behind the blood adherent surface. Outer wall positioning can be automated with motor control as is know in the art or through the use of springs and spring metal alloys as is known in the art. In an embodiment, the wall incorporates illumination. The illumination can be LED, OLED, variably transparent components and/or others as is known in the art. Illumination provides both absorption and excitation characteristics that serve to distinguish constituent reactant response to serum constituents.

Constituent reactants are known in the art and many have been in use for decades, or were used then replaced with newer technologies. They can include, but are not limited to, antibody assays, chemoluminescent assays, chemical assays, aptameric assays, and others known in the art. Response indication can be obtained from, but is not limited to, enzyme reactions, colorimetric changes, fluorescence, luminescence, light wave velocity dispersion, and the like known in the art. Constituent interfacing with the reactant can include, but is not limited to, hydrophilic moieties, hydrophobic moieties, steric hindrance, surface tension, lateral flow membranes, gravity, and any combination as is know in the art.

Reactants respond to serum constituents indicating the presents, absence, or quantity of molecules, structures, accumulations, atoms and the like know in the art to be associated with health or health maladies. Said reactants serve a contextual indicator, both individually and as a group, for information transformation. Information is transformation into a contextual structure that the unskilled end user understands. The contextual indicator/s are used as data inferences for contextual structure instantiation. The reactants maybe general system level indicators, organ level indicators, cellular level indicators, or a combination.

Figure 1:
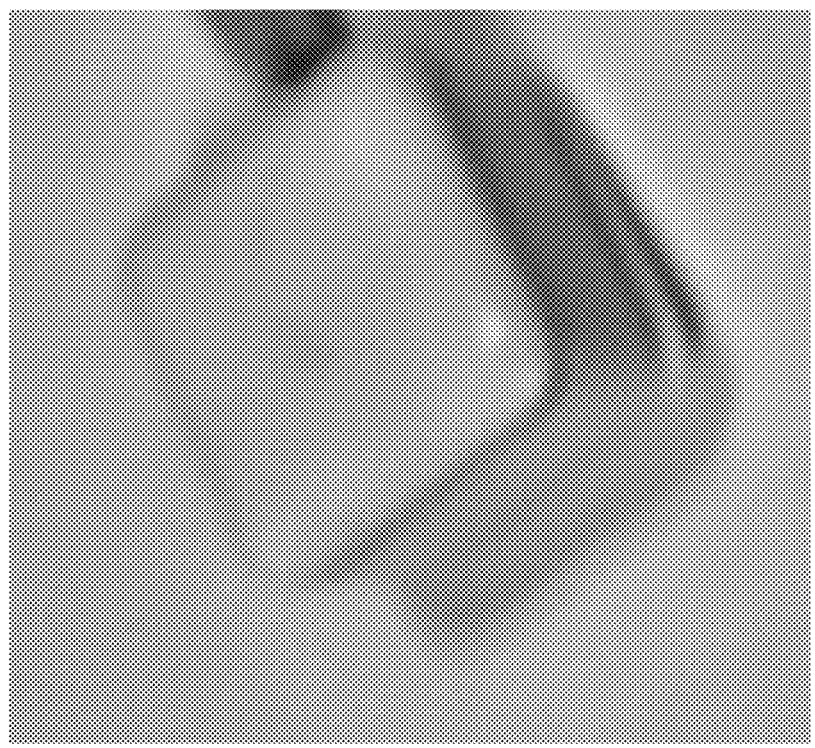
FIG. 1 is a photo of the photonic sensing means having an embedded processor and audio jack or Blutooth or Wi-Fi means for transmitting data from photonic sensor means to the cell phone.

The sensor collects light directly from the response mechanism and/or indirectly through illumination. FIG. 1 is a photo of the means for collecting the data and transmitting that data to a cell phone. Said sensor may be a single pixel, a 2D array of pixels, a 3D array of pixels, or a combination. Photonic results are analog-to-digital converted, as is known in the art, and digital conversions offloaded directly to an embedded processor or logic, and/or transmitted through an interface. Said interface would be an audio jack or Bluetooth in the case of the cell phone instant invention or other interfaces as is known in the art for the kiosk invention.

The embedded processor or the cell phone process receives the information relating to reactants. A mathematical algorithm with apriori reactant information, uses that information along with newly received information to 1) parse the contextual indicators with the newly received information, and 2) use the combined parsed and newly received information to instantiate a contextual structure. Said contextual structure is then abstracted to a level equivalent to the end user's understanding. The end user may, at their discretion, enter an indicator relating to the level of complexity desired.

Said information transform, the abstraction information, is then displayed in the kiosk or cell phone graphic display. That contextual construct can range from, but is not limited to, 'you are healthy' to 'your xxx is abnormal see a physician'. The sample collection, processing, billing, and information display are conducted at a kiosk in a store at a very low cost. The combination of machines, instrumentation, and transformation yields a system of acquiring information and addressing health care issues that currently does not exist but will lower health care costs when implemented.

Figure 2:
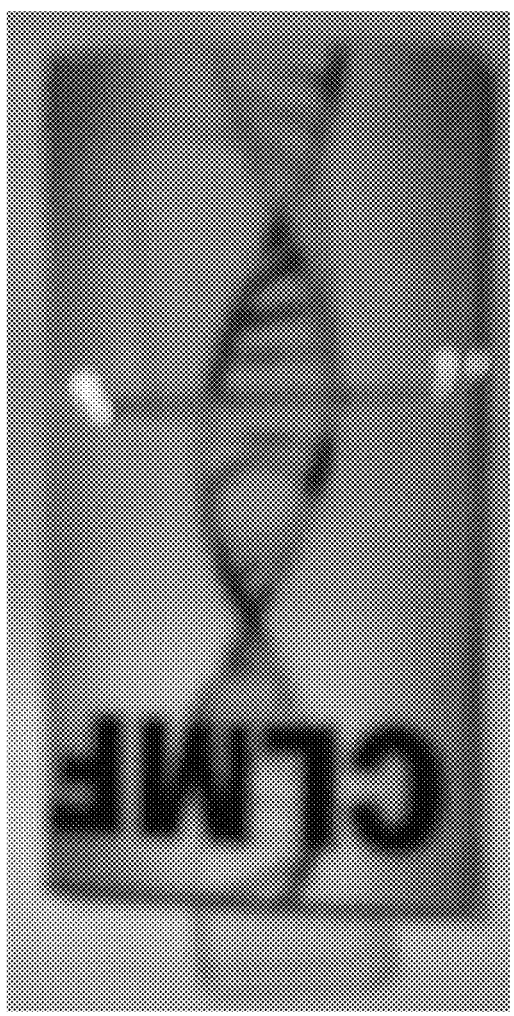
FIG. 2 is a photo of the transparent means having sieving means to remove substantially all nucleated cells from said sample.

A transparent means (FIG. 2) with sieving means is constructed to selectively remove substantially all of the nuclei from a whole blood sample using size exclusion thereby removing the background of large dense nuclei and leaving behind the smaller dense parasites. Parasites such as malaria are smaller than RBCs and often reside within them. Normal RBC are approximately seven microns in diameter and approximately half that for thickness. WCBs are substantially larger and thicker. Size selective methods known in the art are used to remove substantially all the large nucleated WBCs; for which the high density background that algorithms and optics have a difficult time discerning a parasite from a nuclei. A manual collection of a drop of whole blood and its application to a diagnostic means is CLIA waiverable. When a manual means is provided to size sieve for parasites and RBCs with parasites, the parasite concentration increases relative to WBC nuclei. The resulting invention decreases the software overhead and detection requirements because the sample has been processed to concentrate parasites for detection. The embodiment enables cloud linkage, simplifies the process, enables simplifier diagnosis, and lowers cost. Skilled personnel are not required and the embodied method instantiates a business that includes be billed.

In an additional embodiment said sample can come in contact with a parasite indicator means that will further highlight the parasite for a faster simpler diagnostic. That indicator could be fluorescent.

In an additional embodiment said sample can come in contact with a RBC lysate means to further remove background caused by RBC membranes and intracellular constituents that are not parasitic.

It will be recognized by those skilled in the art that changes may be made to the above-described embodiments of the invention without departing from the broad inventive concepts thereof. It is understood therefore, that this invention is not limited to the particular embodiment disclosed, but is intended to cover any modifications that are within the scope and spirit of the invention as defined by the appended claims.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

I claim:

1. A health care business method involving peripheral blood sampling by unskilled personnel, separate photonic detection means with derived information displayed on a cell phone and billing for the services comprising:

a peripheral blood sample is manually collected by sticking a finger, the peripheral blood sample is distributed onto a blood adherent surface, the blood adherent surface having one or more reactants, the reactants respond to the peripheral blood adherent, an illumination source illuminating a photonic sensor, the blood adherent surface with adherent peripheral blood and the reactants, interposed between the illumination source and photonic sensor, the photonic sensor receiving both unchanged illumination from the illumination source and illumination changed by the reactants, data is transferred from the photonic sensor to a cell phone by audio jack or BLUETOOTH or WI-FI means, and analyzed using an algorithm for cardiac tests, thyroid tests, and cancer tests to transform data into diagnostic information; and the information is displayed on a cell phone.

2. The business method of claim 1 being Clinical Laboratory Improvement Amendment (CLIA) waiverable.

3. The business method of claim 1 where the peripheral blood sample includes peripheral blood constituents, the peripheral blood constituents include prostate specific antigen (PSA), vitamins, liver enzymes, and other proteins or molecules.

4. The business method of claim 1 wherein said cell phone is linked to the cloud for diagnosis, storage, billing and other services.

5. The business method of claim 1 wherein said cell phone resides in a store, a retail clinic, assistive care clinic, a facility, or in the home.

6. A health care business method involving peripheral blood sampling by unskilled personnel, separate photonic detection means with derived information displayed on a cell phone and billing for the services comprising:

a peripheral blood sample is manually collected by sticking a finger, the peripheral blood sample is distributed onto a blood adherent surface, the blood adherent surface having one or more reactants, the reactants respond to the peripheral blood adherent, an illumination source illuminating a photonic sensor, the blood adherent surface with adherent peripheral blood and the reactants, interposed between the illumination source and photonic sensor, the photonic sensor receiving both unchanged illumination from the illumination source and illumination changed by the reactants, data is transferred from the photonic sensor to a cell phone by audio jack or BLUETOOTH or WI-FI means, and analyzed using an algorithm or cardiac tests, thyroid tests, and cancer tests to transform the data into diagnostic information, the diagnostic information is transformed into a contextual structure; and the information is displayed on a cell phone.

\* \* \* \* \*